US00PP32057P2

(12) United States Plant Patent
Jones

(10) Patent No.: US PP32,057 P2
(45) Date of Patent: Aug. 11, 2020

(54) SWEET POTATO PLANT NAMED 'ISGHP05-2'

(50) Latin Name: *Ipomoea batatas*
Varietal Denomination: ISGHP05-2

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/501,764

(22) Filed: Jun. 4, 2019

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258, 263.1, 226
CPC ... A01H 5/12; A01H 5/06; A01H 5/02; A01H 5/00; A01H 5/04; A01H 6/00
See application file for complete search history.

(56) References Cited

PUBLICATIONS

Trademark Electronic Search System for Sweet Georgia, retrieved on Feb. 6, 2020, retrieved from the Internet at http://tmsearch.uspto.gov/bin/showfield?f=doc&state=4808:gd0q8i.2.17, one page. (Year: 2020).*

* cited by examiner

*Primary Examiner* — June Hwu
(74) *Attorney, Agent, or Firm* — Cassandra Bright

(57) ABSTRACT

A new and distinct *Ipomoea batatas* cultivar named 'ISGHP05-2' is disclosed, characterized by dark greyed-purple heart-shaped foliage. Plants are semi-compact, have a trailing habit and produce many lateral branches without pinching or chemical growth regulators. The new cultivar is an *Ipomoea batatas*, typically suited for ornamental container and garden use.

2 Drawing Sheets

Latin name of the genus and species: *Ipomoea batatas*.
Variety denomination: 'ISGHP05-2'.

BACKGROUND OF THE INVENTION

The new variety originated as a chance discovery by the inventor, Steve Jones. The variety was discovered as a naturally occurring whole plant mutation from an unnamed, unpatented proprietary variety of *Ipomoea batatas*. The new variety was discovered in August 2018 at a commercial greenhouse in Santa Paula, Calif.

After selecting and isolating the new cultivar, asexual reproduction of the new cultivar 'ISGHP05-2' was first performed by vegetative tip cuttings in a commercial greenhouse in Santa Paula, Calif. in October 2018. 'ISGHP05-2' has since produced several generations and has shown that the unique features of this cultivar are stable and reproduced true to type. Typical asexual reproduction of the new variety is by vegetative tip cuttings.

SUMMARY OF THE INVENTION

The cultivar 'ISGHP05-2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ISGHP05-2'. These characteristics in combination distinguish 'ISGHP05-2' as a new and distinct *Ipomoea* cultivar:

1. Semi-compact, trailing habit.
2. Dark greyed purple foliage.

3. Very well branched.
4. Heart-shaped foliage.

PARENTAL COMPARISON

Plants of the new cultivar 'ISGHP05-2' are similar to the parent in most horticultural characteristics. However, 'ISGHP05-2' differs in the following:

1. The new variety has greater plant vigor than the parent.
2. The new variety has shorter, wider leaves than the parent.

COMMERCIAL COMPARISON

Plants of the new cultivar 'ISGHP05-2' can be compared to the unpatented commercial variety *Ipomoea batatas* SWEET GEORGIA 'Heart Purple'. Plants of 'ISGHP05-2' are similar to plants of SWEET GEORGIA 'Heart Purple' in some horticultural characteristics, however, plants of 'ISGHP05-2' differ in the following:

1. The new variety has greater plant vigor than this comparator.
2. The new variety has smaller, more heart-shaped, less arrow-shaped leaves than this comparator.

BRIEF DESCRIPTION OF THE PHOTOGRAPHS

Figure 1:
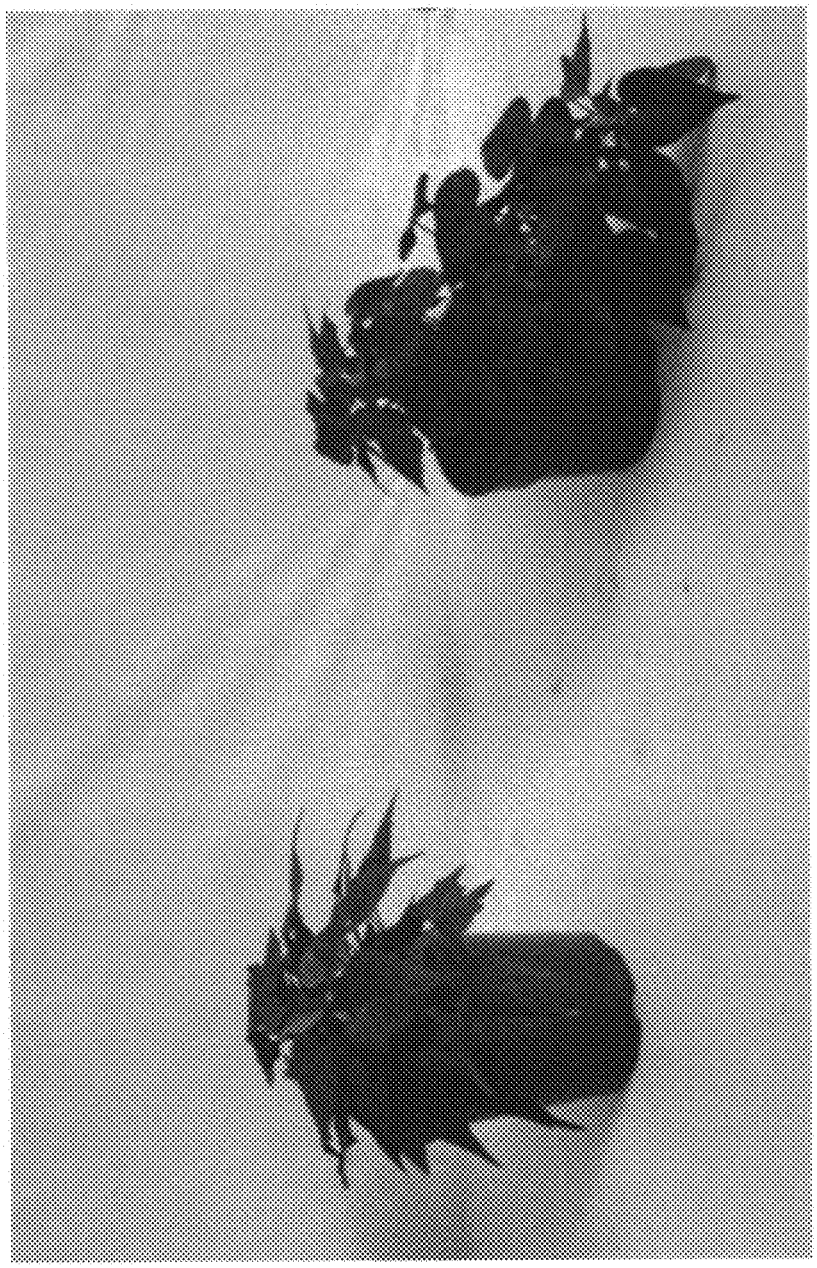

The accompanying photograph in FIG. 1 illustrates in full color a typical plant of 'ISGHP05-2', seen in the right side of the photo. The plant on the left of the photo is the abovementioned comparator variety SWEET GEORGIA 'Heart Purple'. Both plants are approximately 8 weeks old, from an unrooted cutting, shown in a 6 inch pot.

Figure 2:
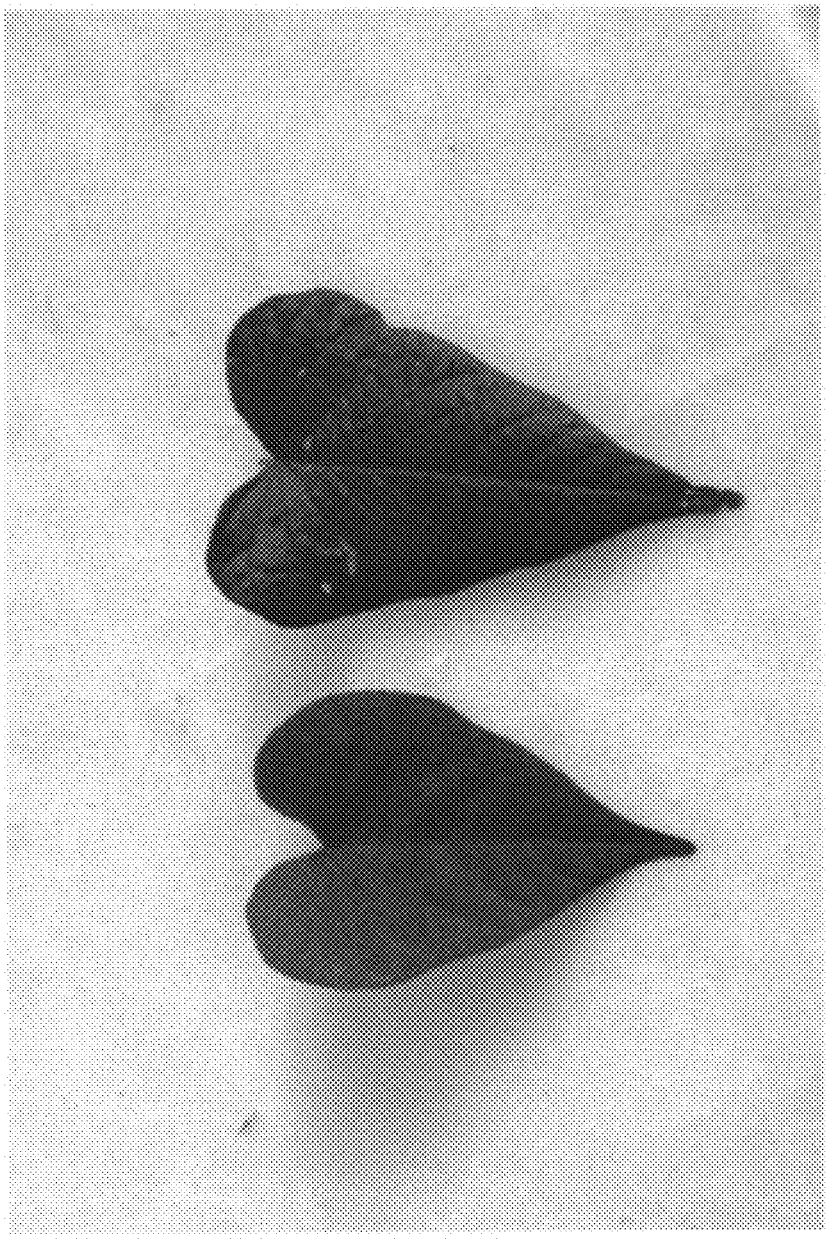

FIG. 2 illustrates a close up of the foliage of both the new variety and the abovementioned comparator. Foliage of the new variety is on the left in FIG. 2, foliage of this comparator is seen on the right side of the photo. Plants were grown in a greenhouse in Santa Paula, Calif.

The photographs were taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2007, except where general terms of ordinary dictionary significance are used. The following observations and measurements describe 'ISGHP05-2' plants grown during the Spring months in a greenhouse in Santa Paula, Calif., under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea batatas* 'ISGHP05-2'.

Age of the plant described: Approximately 20 weeks from an unrooted cutting.

Container size of the plant described: 1 gallon commercial container.

Propagation:

- *Propagation method*.—Terminal tip cuttings.
- *Time to develop roots suitable for transplanting*.—Summer — about 6 days at an average temperature of 24° C.; Winter — about 10 days at an average temperature of 24° C.
- *Root description*.—Thick, fleshy. Roots colored closest to RHS Yellow-White 158A.
- *Tuber description*.—Not observed to date.

Plant:

- *Growth habit*.—Semi-compact, and mounding in center of plant, then trailing with maturity. Dense and bushy.
- *Height*.—Measured from top of soil line of pot, approximately 18 cm.
- *Plant spread*.—Approximately 45 cm.
- *Growth rate*.—Rapid.
- *Branching characteristics*.—Very free branching, alternate or whorled occurring.

Primary lateral branches:

- *Length*.—8 to 25 cm.
- *Diameter*.—Approximately 0.5 cm.
- *Texture*.—Glabrous.
- *Appearance*.—Glossy.
- *Color*.—Near RHS Greyed-Purple N186C.
- *Strength*.—Strong.
- *Internode length*.—0.5-1.2 cm.
- *Adventitious roots at nodes*.—Not observed.
- *Anthocyanin coloration primary lateral branches*.—Moderate.

Secondary lateral branches:

- *Length*.—4 to 8 cm.
- *Diameter*.—Approximately 0.4 cm.
- *Texture*.—Glabrous.
- *Color*.—Near RHS Greyed-Purple N186D.
- *Strength*.—Flexible.
- *Internode length*.—Range between 0.5 to 1.0 cm.
- *Quantity per 20 week old plant*.—Approximately 15 to 25.
- *Adventitious roots at nodes*.—Not observed.

New shoot growth characteristics:

- *Color*.—Near RHS Greyed-Purple N186D.
- *Aspect*.—Upright in center of plant, outward along outer circumference.
- *Texture*.—Glabrous.

Foliage:

Leaf:

- *Arrangement*.—Whorled and alternate, simple.
- *Average length*.—12 cm.
- *Average width*.—9 cm.
- *Shape of blade*.—Cordate.
- *Apex*.—Acute.
- *Base*.—Cordate.
- *Margin*.—Entire.
- *Aspect*.—Mostly flat, slightly undulating.
- *Texture of top surface*.—Glabrous.
- *Texture of bottom surface*.—Glabrous.
- *Appearance of top surface*.—Matte.
- *Appearance of bottom surface*.—Matte.
- *Quantity of leaves per lateral branch*.—Average 5 to 20.

Foliage color:

- *Young foliage upper side*.—Near RHS Greyed-Purple N186A flushed near veins N187C. Veins N186C.
- *Young foliage under side*.—Near RHS Greyed-Purple N186B flushed near veins N187C. Veins N187C.
- *Mature foliage upper side*.—Near RHS Greyed-Purple N186A. Veins N186C.
- *Mature foliage under side*.—Near RHS Greyed-Purple N186C. Veins 187B.

Venation:

- *Type*.—Palmate, reticulate.

Petiole:

- *Length*.—Average range 7 to 12 cm.
- *Diameter*.—Approximately 0.3 cm.
- *Texture*.—Glabrous.
- *Appearance*.—Glossy.
- *Color*.—Near RHS Greyed-Purple 187A.
- *Strength*.—Moderately strong, very flexible.
- *Aspect*.—Straight to slightly undulate.
- *Anthocyanin coloration*.—Moderate.

Flower: Flowering not observed to date.

Other characteristics:

Seeds and fruits: No seeds/fruits observed.

Disease/pest resistance: Neither resistance nor susceptibility to the normal pests and diseases of *Ipomoea* has been observed.

Temperature tolerance: Tolerates low temperatures to approximately 2° C. Good high temperature tolerance, observed to at least 38° C.

What is claimed is:

1. A new and distinct cultivar of Ornamental Sweet Potato Plant Named 'ISGHP05-2' as herein illustrated and described.

* * * * *